United States Patent [19]

Fanshawe et al.

[11] 3,957,805

[45] May 18, 1976

[54] SUBSTITUTED PYRIDINES AND DIAZINES AND METHODS OF PREPARING THE SAME

[75] Inventors: William Joseph Fanshawe; Gretchen Ellen Wiegand, both of Pearl River; Lantz Stephen Crawley, Spring Valley, all of N.Y.; Sidney Robert Safir, River Edge, N.J.

[73] Assignee: American Cyanamid Company, Stamford, Conn.

[22] Filed: July 24, 1974

[21] Appl. No.: 491,449

[52] U.S. Cl................................ 260/296 R; 424/250; 424/251; 424/263; 260/250 A; 260/250 B; 260/250 Q; 260/256.4 R
[51] Int. Cl.².......................................... C07D 213/42
[58] Field of Search.................... 260/307 H, 296 R

[56] References Cited
OTHER PUBLICATIONS

Jacquier et al., Chemical Abstracts, Vol. 71, abst. 112,846c (1969).

*Primary Examiner*—John D. Randolph
*Attorney, Agent, or Firm*—Norton S. Johnson

[57] ABSTRACT

The preparation of cyclopropylisoxazolylpyridines and cyclopropylisoxazolyldiazines from corresponding cyclopropyl monooximes is described. The products are useful in the treatment of pain, muscle spasm, inflammation, anxiety, or tension.

26 Claims, No Drawings

SUBSTITUTED PYRIDINES AND DIAZINES AND METHODS OF PREPARING THE SAME

DESCRIPTION OF THE INVENTION

This invention relates to new cyclopropylisoxazolyl-pyridines and cycloproplyisoxazolyldiazines which may be illustrated by the following formula:

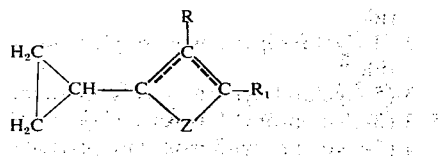

where R is selected from a group consisting of hydrogen, lower alkyl, lower cycloalkyl and phenyl and $R_1$ is selected from a group consisting of pyridyl, pyrazinyl, pyridazinyl, pyrimidinyl, and quinoxalinyl, and wherein Z is a trivalent radical selected from the group consisting of A and B

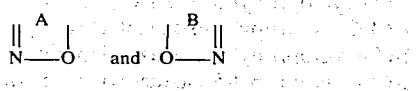

and the dotted line represents one double bond, the position of which is dependent upon the definition of Z. When Z is B, the double bond is adjacent to the cyclopropyl substituent and when Z is A, the double bond is in the other position with the proviso that when Z is B, R is as defined and $R_1$ is pyridyl, the carbon to carbon double bond may also be absent. The term "lower" as used in lower alkyl is intended to include those having 1 to 6 carbon atoms and in lower cycloalkyl those having 3 to 6 carbon atoms.

This invention also relates to monoximes of the following formula:

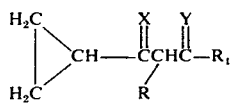

wherein X and Y are O or NOH, such that when X is O, Y is NOH and when X is NOH, Y is O. R and $R_1$ are as defined above. These monooximes are useful intermediates in the preparation of the aforementioned cyclopropylisoxazolylpyridines and cyclopropylisoxazolyldiazines.

Pharmaceutically acceptable acid addition salts of the cyclopropylisoxazolylpyridines and cyclopropylisoxazolinyldiazines are considered to be within the purview of the present invention and can be prepared by direct neutralization of the free bases with the appropriate acid. These salts are those in which the anion does not contribute significant toxicity to the salt in the dosages thereof enployed in accordance with the present invention. Examples of suitable salts are the acetate, propionate, butyrate, pamoate, mucate, citrate, maleate, tosylate, phosphate, nitrate, sulfate, hydrobromide, hydroiodide, hydrochloride, etc.

The cyclopropylisoxazolylpyridines and diazines of the present invention may be prepared by either of two general reaction sequences. In the first reaction reference (Process A), a ketone such as cyclopropylmethylketone is condensed with a pyridyl or diazinylcarboxylic acid ester in the presence of a base, such as sodium methoxide, in a non-polar solvent, such as benzene or toluene, at a temperature of 80° to 110°C. for a period of 1 to 24 hours to provide a 1-cyclopropyl-3-pyridyl (or diazinyl)-1,3-propanedione. The 1-cyclopropyl-3-pyridyl (or diazinyl)-1,3-propanedione is reacted with a hydroxylamine salt, such as the hydrochloride, in a polar solvent, such as ethanol, at a temperature of 25° to 80°C. for a period of 1 hour to 24 hours with the addition of a base, such as triethylamine to provide a mixture of isomeric monooximes The mixture of monooximes is treated with an excess of an acidic reagent such as ethanolic hydrogen chloride or sulfuric acid, neat, or in the presence of a solvent such as methylene chloride to furnish a mixture of the isomeric cyclopropylisoxazolylpyridines or diazines. The mixture of isomeric isoxazoles can then be separated into the individual components by physical or chemical procedures as described in the Examples. In the case of those mixtures or monoximes where $R_1$ is 2-pyridyl, pyrazinyl or 3-pyridazinyl, treatment with a catalytic amount of the above acid reagent furnishes the 5-cyclopropyl-3-isoxazolylpyridine or 5-cyclopropyl-3-isoxazolyldiazine as the exclusive product.

PROCESS A

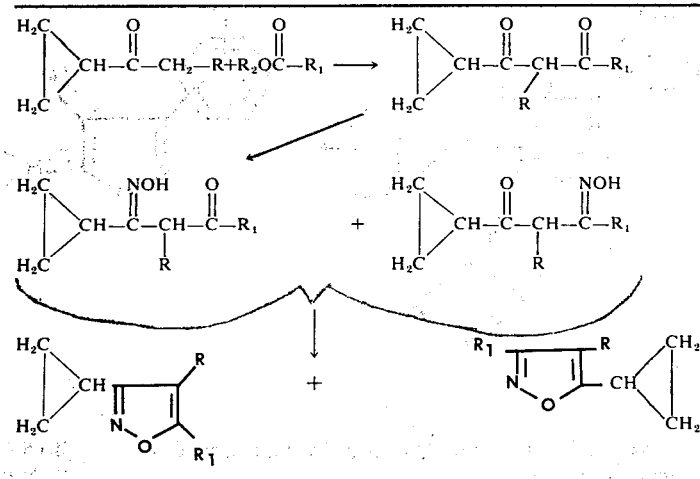

R and $R_1$ are as hereinbefore defined and $R_2$ is lower alkyl.

In the second reaction sequence (Process B), an enamine of a cyclopropylketone such as 1-(1-cyclopropylvinyl)-pyrrolidine (or other enamine bases, like morpholine or piperidine) is reacted with a pyridylcarbohydroxamoyl chloride salt such as the hydrochloride in a polar solvent such as ethanol in the presence of a base such as triethylamine at a temperature between 0° – 25°C. to furnish a [5-cyclopropyl-5-(1-pyrrolidinyl)-2-isoxazolin-3-yl]pyridine. The latter is treated with a strong acid such as perchloric acid in a polar solvent such as ethanol to furnish a (5-cyclopropyl-3-isoxazolyl)-pyridine.

Alternatively, reaction of a pyridylcarbohydroxamoyl chloride salt such as the hydrochloride with cyclopropylacetylene in a polar solvent such as ethanol in the presence of a base such as triethylamine at a temperature of 0°–25°C. can furnish directly a (5-cyclopropyl-3-isoxazolyl)pyridine.

A further method for preparing a (5-cyclopropyl-3-isoxazolyl)pyridine consists of reacting an oxime such as pyridinecarboxaldehyde oxime with an alkyne such as cyclopropylacetylene in the presence of an oxidizing agent such as lead tetraacetate at a temperature of −78° to 0°C. in a solvent such as methylene chloride.

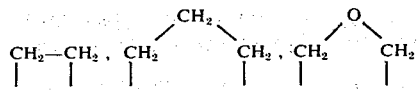

and $R_3$ is hydrogen or lower alkyl.

Among compounds within the scope of the present invention are, for example, 2-(5-Cyclopropyl-3-isoxazolyl)pyridine hydrochloride
2-(3-Cyclopropyl-5-isoxazolyl)pyridine hydrochloride
3-(5-Cyclopropyl-3-isoxazolyl)pyridine
3-(3-Cyclopropyl-5-isoxazolyl)pyridine
4-(5-Cyclopropyl-3-isoxazolyl)pyridine
4-(3-Cyclopropyl-5-isoxazolyl)pyridine
6-Methyl-2-(5-cyclopropyl-3-isoxazolyl)pyridine
6-Methyl-2-(3-cyclopropyl-5-isoxazolyl)pyridine
2-(5-Cyclopropyl-3-isoxazolyl)pyrazine
2-(3-Cyclopropyl-5-isoxazolyl)pyrazine
3-(5-Cyclopropyl-3-isoxazolyl)pyridazine
3-(3-Cyclopropyl-5-isoxazolyl)pyridazine
4-(5-Cyclopropyl-3-isoxazolyl)pyridazine
4-(3-Cyclopropyl-5-isoxazolyl)pyridazine
2-(5-Cyclopropyl-3-isoxazolyl)pyrimidine
2-(3-Cyclopropyl-5-isoxazolyl)pyrimidine

PROCESS B

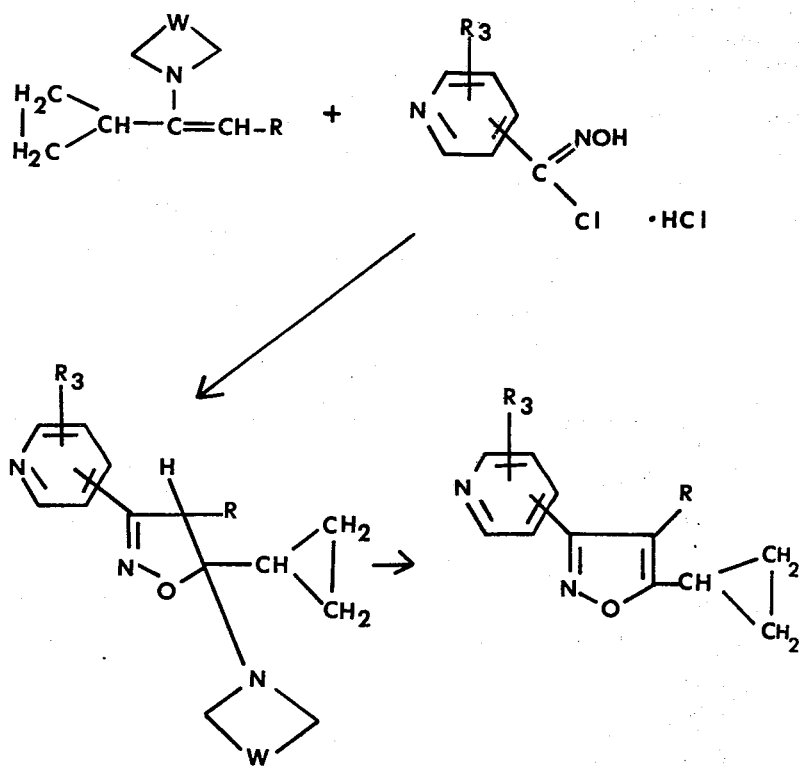

R is as previously defined; W is a divalent radical of the group consisting of 4-(5-Cyclopropyl-3-isoxazolyl)pyrimidine
4-(3-Cyclopropyl-5-isoxazolyl)pyrimidine 5-(5-Cyclopropyl-3-isoxazolyl)pyrimidine
2-(5-Cyclopropyl-4-methyl-3-isoxazolyl)pyridine
2-(4,5-Dicyclopropyl-3-isoxazolyl)pyridine
3-(5-Cyclopropyl-4-methyl-3-isoxazolyl)pyridine
3-(4,5-Dicyclopropyl-3-isoxazolyl)pyridine
3-(5-Cyclopropyl-4-phenyl-3-isoxazolyl)pyridine
4-(5-Cyclopropyl-4-ethyl-3-isoxazolyl)pyridine
2-(5-Cyclopropyl-3-isoxazolyl)quinoxaline
2-(5-Cyclopropyl-4-methyl-3-isoxazolyl)pyrazine
3-(4,5-Dicyclopropyl-3-isoxazolyl)pyridazine
4-(5-Cyclopropyl-4-phenyl-3-isoxazolyl)pyrimidine
2-(5-Cyclopropyl-4-ethyl-3-isoxazolyl)quinoxaline
4-(5-Cyclopropyl-2-isoxazolin-3-yl)pyridine
3-(5-Cyclopropyl-2-isoxazolin-3-yl)pyridine
2-(5-Cyclopropyl-4-methyl-2-isoxazolin-3-yl)pyridine
3-(4,5-Dicyclopropyl-2-isoxazolin-3-yl)pyridine
4-(5-Cyclopropyl-4-phenyl-2-isoxazolin-3-yl)pyridine
1-Cyclopropyl-3-(2-pyrazinyl)-1,3-propanedione, 3-oxime
1-Cyclopropyl-3-(2-pyrazinyl)-1,3-propanedione, 1-oxime
1-Cyclopropyl-3-(3-pyridazinyl)-1,3-propanedione, 3-oxime
1-Cyclopropyl-3-(3-pyridazinyl)-1,3-propanedione, 1-oxime
1-Cyclopropyl-3-(3-pyridyl)-1,3-propanedione, 3-oxime
1-Cyclopropyl-3-(3-pyridyl)-1,3-propanedione, 1-oxime
1-Cyclopropyl-3-(4-pyridyl)-1,3-propanedione, 3-oxime
1-Cyclopropyl-3-(4-pyridyl)-1,3-propanedione, 1-oxime
1-Cyclopropyl-2-methyl-3-(2-pyrazinyl)-1,3-propanedone, 3-oxime
1,2-Dicyclopropyl-3-(3-pyridyl)-1,3-propanedione, 3-oxime
1-Cyclopropyl-2-phenyl-3-(4-pyridyl)-1,3-propanedione, 3-oxime
2-[5-Cyclopropyl-5-(1-pyrrolidinyl)-2-isoxazolin-3-yl]pyridine
3-[5-Cyclopropyl-5-(1-pyrrolidinyl)-2-isoxazolin-3-yl]pyridine
4-[5-Cyclopropyl-5-(1-pyrrolidinyl)-2-isoxazolin-3-yl]pyridine
2-(5-Cyclopropyl-2-isoxazolin-3-yl)pyridine
3-(5-Cyclopropyl-2-isoxazolin-3-yl)pyridine hydrochloride
4-(5-Cyclopropyl-2-isoxazolin-3-yl)pyridine.
2-Chloro-3-(5-cyclopropyl-3-isoxazolyl)pyridine The compounds of this invention show anti-axiety and muscle relaxant activity by their ability to protect warm blooded animals, e.g., rats from convulsions resulting from the administration of pentylenetetrazol. Graded dose levels of the compounds are administered orally in a 2% starch vehicle to groups of at least five rats. At the estimated time of peak effect, the rats are treated intravenously with pentylenetetrazol at a dose of 21 to 23 mg/kg. This dose is estimated to cause clonic seizures in 99% of unprotected rats. The median effective dose is calculated by the method of J. T. Litchfield and F. Wilcoxon [J. Pharmacol, Exp. Ther., 96 99 (1949)]. These data on representative compounds of this invention are summarized in Table I. It has been reported [R. T. Hill and D. M. Tedeschi, "Animal Testing and Screening Procedures in Evaluating Psychotropic Drugs", in An Introduction to Psychopharmacology, Eds. R. R. Rech and K. E. Moore, Raven Press, New York, 1971 pp 237–288] that there is a high degree of correlation between anticonvulsant effects in rodents and antianxiety effects in higher warm-blooded animals. The following Table I shows the median effective dose of representative compounds of this invention when subjected to the above test.

TABLE I

Protection Against Clonic Seizures Caused by Pentylenetetrazol in Rats

| Compound | Median Effective Dose mg/kg orally |
|---|---|
| 4-(5-cyclopropyl-3-isoxazolyl)pyridine | 36 |
| 3-(5-cyclopropyl-3-isoxazolyl)pyridine | 25 |
| 2-(5-cyclopropyl-3-isoxazolyl)pyridine hydrochloride | 72 |
| 2-(5-cyclopropyl-3-isoxazolyl)pyrazine | 14 |
| 3-(5-cyclopropyl-3-isoxazolyl)pyridazine | 20 |
| 4-(5-cyclopropyl-3-isoxazolyl)pyrimidine | 89 |
| 2-(5-cyclopropyl-3-isoxazolyl)-quinoxaline | 120 |
| 3-(5-cyclopropyl-2-isoxazolin-3-yl)pyridine hydrochloride | 36 |
| 4(5-cyclopropyl-2-isoxazolin-3-yl)pyridine | 150 |

The compounds of this invention are also useful for the relief of pain and inflammation in warm-blooded animals. To determine analgesic activity, a modification of the method of Randall and Selitto [Arch. int. Pharmacodyn., 111, 409 (1957)] is used. This test measures the pain threshold of rats whose paws are made sensitive to pressure by the injection of a 20% aqueous suspension (0.1 ml) of brewers' yeast into the plantar surface of the left hind paw. Constantly increasing force (16 grams/second) is applied to the swollen paw using an Analgesy Meter, Ugo Basile. The pressure is cut off at 250 grams of force when there is no response (sudden struggle or vocalization). Control rats treated with the starch vehicle respond to a pressure or force of about 30 grams. Pressure-pain thresholds are always recorded two hours after brewers' yeast. Analgesic agents are administered at the same time as the yeast, at a dose of 200 mg/kg orally. Ratios of treated (T)/control (C) reaction thresholds are calculated as estimates of analgesic efficacy (degree of analgesia attainable). Potency is regarded as the dose necessary to produce a given level of analgesia (i.e. 100% elevation of pain threshold is T/C=2.0). Table II gives the results obtained with representative compounds.

TABLE II

Analgesic Protection Versus Pain Induced by Brewer's Yeast in the Rat Paw

| COMPOUND | RATIO (TREATED/CONTROL) MEASURED AT 2 HRS FOLLOWING 200 MG/KG ORAL DOSE |
|---|---|
| 4-(5-Cyclopropyl-3-isoxazolyl)pyridine | 6.8 |
| 3-(3-Cyclopropyl-5-isoxazolyl)pyridine | 3.2 |
| 3-(5-Cyclopropyl-3-isoxazolyl)pyridine | 5.8 |

TABLE II -continued

Analgesic Protection Versus Pain Induced by Brewer's Yeast in the Rat Paw

| COMPOUND | RATIO (TREATED/CONTROL) MEASURED AT 2 HRS FOLLOWING 200 MG/KG ORAL DOSE |
|---|---|
| 2-(5-Cyclopropyl-3-isoxazolyl)pyridine hydrochloride | 10.0 |
| 2(3-Cyclopropyl-5-isoxazolyl)pyridine hydrochloride | 2.2 |
| 2-(5-Cyclopropyl-3-isoxazolyl)pyrazine | 2.5 |
| 3-(5-Cyclopropyl-3-isoxazolyl)pyridazine | 3.9 |
| 4-(5-Cyclopropyl-3-isoxazolyl)pyrimidine | 2.2[a] |
| Aspirin | 2.1 |

[a]100 mg/kg oral

In determining the acute antiinflammatory activity of the present compounds Royal Hart, Wistar strain rats ranging from 80 to 90 g. are used. The rats are fasted overnight prior to dosing but have free access to water. The drugs in aqueous supension are administered by gavage in a volume of 1.7 ml./50 g. rat (corresponds to hydration volume used by Winter et al., Proc. Soc. Exp. Biol & med. 111, 544–547, 1962). The dosage of all compounds is 250 mg./kg.

The phlogistic agent used is carrageenin prepared as a sterile 1% suspension in 0.9% sodium chloride for routine testing. A volume of 0.05 ml. is injected through a 26 gauge needle into the plantar tissue of the right hind paw. Measurements are made 5 hours after drug administration (4 hours after carrageenin challenge) unless otherwise indicated.

Volumes of both the normal and carrageenin inflamed feet are determined. The differences between the two measurements is considered to be the increased edema due to the carrageenin administration. Results are expressed as a Control (C)/Treated (T) efficacy ratio. The ratio of mean edema volume of eight control rats over the mean edema volume of two treated rats). If the C/T is equal or greater than 1.41, the test is repeated a second time. If the mean ratio of test 1 and 2 is equal or greater than 1.43 the compound is accepted as active. The following Table III summarizes the results obtained with representative compounds.

TABLE III

THE EFFECTS OF ANTI-INFLAMMATORY AGENTS ON CARRAGEENIN INDUCED EDEMA OF THE RAW PAW

| COMPOUND | RATIO (CONTROL/TREATED EDEMA) MEASURED AT 5 HRS AFTER 250 MG/KG ORAL DOSE |
|---|---|
| 4-(5-Cyclopropyl-3-isoxazolyl)pyridine | 3.05 |
| 4-(3-Cyclopropyl-5-isoxazolyl)pyridine | 2.75 |
| 3-(5-Cyclopropyl-3-isoxazolyl)pyridine | 2.19[a] |
| 2-(5-Cyclopropyl-3-isoxazolyl)pyridine hydrochloride | 2.69 |
| 2-(3-Cyclopropyl-5-isoxazolyl)pyridine hydrochloride | 3.72 |
| 2-(5-Cyclopropyl-3-isoxazolyl)pyrazine | 3.14 |
| 2-(3-Cyclopropyl-5-isoxazolyl)pyrazine | 1.85 |
| 3-(5-Cyclopropyl-3-isoxazolyl)pyridazine | 3.04 |
| 3-(3-Cyclopropyl-5-isoxazolyl)pyridazine | 1.81 |
| Aspirin | 2.80 |

[a]125 mg/kg oral dose

The compounds of this invention also show antipyretic activity by their ability to reduce a hyperthermic response in warm-blooded animals, e.g., rats, induced by the subcutaneous injection of a suspension of brewers' yeast. This is a modification of the method described by Teotino, et al., J. Med. Chem. 6, 248 (1963). A 40% suspension of brewer's yeast in distilled water is administered to groups of 5 to 10 rats subcutaneously (1.0 ml./100 g. of body weight). Eighteen hours later, rectal temperatures are recorded and compounds, control vehicle (2% starch suspension) or aspirin is administered. Rectal temperatures are recorded 4 hours later and the results are compared with the starch treated controls and with aspirin, a reference antipyretic agent. The results using representative compounds are given in Table IV.

TABLE IV

Antipyretic Activity Against Brewers' Induced Hyperthermia in Rats

| Compound | Mean Δ°F. from Starch-treated controls at 4 Hrs. following 50 mg./kg. Oral dose | |
|---|---|---|
| | Compound | Aspirin, 200 mg./kg. |
| 4-(5-Cyclopropyl-3-isoxazolyl)-pyridine | −6.1 | −5.6 |
| 4-(3-Cyclopropyl-5-isoxazolyl)-pyridine | −3.6 | −1.0 |
| 3-(3-Cyclopropyl-5-isozazolyl)-pyridine | −3.9 | −1.0 |
| 3-(5-Cyclopropyl-3-isoxazolyl)-pyridine | −4.2 | −2.7 |
| 2-(5-Cyclopropyl-3-isoxazolyl)-pyridine hydrochloride | −5.0 | −5.6 |
| 2-(3-Cyclopropyl-5-isoxazolyl)-pyridine hydrochloride | −2.0 | −1.0 |
| 2-(5-Cyclopropyl-3-isoxazolyl)-pyrazine | −5.2 | −2.7 |

The active components of this invention can be used in compositions such as tablets; the principal active ingredient is mixed with conventional tableting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositons of the present invention may be incorporated for administration include suitably flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The dosage may vary from 1 mg. to 70 mg. per kg. of warm-blooded animal per day, preferably in multiple doses. The daily dosage requirement may be from 50 mg. to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

DETAILED DESCRIPTION

The examples which follow describe the preparation of representative compounds of the present invention.

EXAMPLE 1

Preparation of
1-Cyclopropyl-3-(4-pyridyl)-1,3-propanedione

A mixture of 13.7 g. of methyl isonicotinate, 16.8 g. of cyclopropylmethyl ketone and 6 g. of sodium methoxide in 150 ml. of benzene is heated under reflux for 8 hours. The mixture is filtered and the collected solid is dissolved in water. The aqueous mixture is made weakly acidic with dilute hydrochloric acid and extracted with ether. The ethereal solution is dried over magnesium sulfate and concentrated under reduced pressure to give 1-cyclopropyl-3-(4-pyridyl)-1,3-propanedione as a mobile, yellow liquid, infra-red sectrum $6.15\mu$ (CHCl$_3$, $\beta$-diketone).

EXAMPLES 2 and 3

Preparation of 4-(5-Cyclopropyl-3-isoxazolyl)pyradine and 4-(3-Cyclopropyl-5-isoxazolyl)pyridine To a stirred mixture of 47 g. of 1-cyclopropyl-3-(4-pyridyl)-1,3-propanedione, 26.7 g. of hydroxylamine hydrochloride, 290 ml. of ethanol, and 190 ml. of water is added slowly 26.7 g. of sodium carbonate. This solution is heated under reflux for 16 hours and the ethanol is evaporated under reduced pressure. The residue is diluted with 200 ml. of water and the aqueous mixture is extracted with chloroform. The chloroform solution is dried over magnesium sulfate and concentrated to a solid. Recrystallization from benzne-hexane gives cream-colored crystals, melting point 75°–80°C., which is a mixture of 4-(5-cyclopropyl-3-isoxazolyl)pyridine and 4-(3-cyclopropyl-5-isoxazolyl)pyridine. Treatment of this mixture by liquid-liquid partition chromatography on a diatomaceous earth column with a heptane-acetonitrile-water system permits the separation of the components; namely, 4-(5-cyclopropyl-3-isoxazolyl)-pyridine as white crystals, melting point 81°–84°C., nmr spectrum $\delta 6.84$ (DMSO-d$_6$, s, 4-isoxazolyl H); and 4-(3-cyclopropyl-5-isoxazolyl)-pyridine, as off-white crystals, melting point 102°–108°C., nmr spectrum $\delta 7.02$ (DMSO-d, s, 4-isoxazolyl H).

The 4-(5-cyclopropyl-3-isoxazolyl)pyridine forms a slightly water soluble citrate salt and 4-(3-cyclopropyl-5-isoxazolyl)pyridine forms a water soluble phosphate salt when treated with phosphoric acid.

EXAMPLES 4 and 5

Preparation of
3-Amino-3-cyclopropyl-1-(4-pyridyl)-2-propen-1-one and 4-(5-Cyclopropyl-3-isoxazolyl)pyridine A 1.0 g. sample of the mixture of 4-(5-cyclopropyl-3-isoxazolyl)pyridine and 4-(3-cyclopropyl-5-isoxazolyl)pyridine, obtained as described in Examples 2 and 3, is mixed with 0.125 g. of platinum oxide and 75 ml. of ethanol. This mixture is treated with hydrogen on a Parr apparatus at 40 psi for 2 hours at room temperature. The mixture is filtered and the filtrate concentrated to yield a solid. Recrystallization from ethyl acetate-petroleum ether (30°–60°C.) provides 3-amino-3-cyclopropyl-1-(4-pyridyl)-2-propen-1-one as white crystals, melting point 124°–125°C. The ethyl acetate-petroleum ether (30°–60°C.) filtrate is concentrated to a solid which is recrystallized from aqueous ethanol to give 4-(5-cyclopropyl-3-isoxazolyl)pyridine as white crystals, melting point 78°–79.5°C., mmr spectrum $\delta 6.85$ (DMSO-d$_6$, s, 4-isoxazolyl H).

EXAMPLE 6

Preparation of
4-[5-Cyclopropyl-5-(1-pyrrolidinyl)-2-isoxazolin-3-yl]pyridine

To a stirred solution of 60 g. of triethylamine and 88 g. of 1-(1-cyclopropylvinyl)-pyrrolidine in 750 ml. of ethanol is added 40.5 g. of isonicotinoyl chloride, oxime hydrochloride in small portions during 100 minutes at room temperature. The ethanol is evaporated under reduced pressure and the oily residue is mixed with water. The aqueous mixture is extracted with ether, the ethereal solution dried over sodium sulfate and concentrated under reduced pressure to yield a brown solid, which is recrystallized from benzene-hexane to furnish straw-colored crystals, melting point 80°–85°C.

EXAMPLE 7

Preparation of 4-(5-Cyclopropyl-3-isoxazolyl)pyridine

To a solution of 2.6 g. of 4-[5-cyclopropyl-5-(1-pyrrolidinyl)-2-isoxazolin-3-yl]pyridine in 25 ml. of ethanol is added 1.4 g. of 70% perchloric acid dissolved in 5 ml. of ethanol. This solution is diluted wth 25 ml. of water and heated on a steam bath for 1.0 hour. The solution is poured onto cracked ice, made basic with 10 N sodium hydroxide and filtered to collect straw-colored crystals, melting point 76°–80°C., nmr spectrum δ6.84 (DMSO-$d_6$, s, 4-isoxazolyl H).

EXAMPLE 8

Preparation of 1-Cyclopropyl-3-(3-pyridyl)-1,3-propanedione

A mixture of 39 g. of ethyl nicotinate, 33 g. of cyclopropylmethyl ketone and 18 g. of sodium methoxide in 400 ml. of benzene is heated under reflux for 6 hours. The mixture is diluted with 400 ml. of water and the benzene phase is separated. The aqueous phase is made weakly acidic with dilute hydrochloric acid and extracted with chloroform. The chloroform solution is dried over magnesium sulfate and concentrated under reduced pressure to give a solid. This solid is recrystallized from hexane to give colorless crystals, melting point 69°–70°C.

EXAMPLES 9 and 10

Preparation of 1-Cyclopropyl-3-(3-pyridyl)-1,3-propanedione, 1-Oxime and 1-Cyclopropyl-3-(3-pyridyl)-1,3-propanedione, 3-Oxime A solution of 1.9 g. of 1-cyclopropyl-3-(3-pyridyl)-1,3-propanedione, 0.7 g. of hydroxylamine hydrochloride and 2.0 g. of triethylamine in 25 ml. of ethanol is heated under reflux for 5 hours. The solution is concentrated under reduced pressure and the residue is mixed with water. The aqueous mixture is extracted with chloroform, the chloroform solution dried over magnesium sulfate and concentrated under reduced pressure to give an oily solid. This solid is recrystallized from acetonitrile to give white crystals, melting point 114°–117°C.

EXAMPLES 11 and 12

Preparation of 3-(5-Cyclopropyl-3-isoxazolyl)pyridine and 3-(3-Cyclopropyl-5-isoxazolyl)pyridine To 2.0 ml. of concentrated sulfuric acid is added slowly 0.33 g. of 1-cyclopropyl-3-(3-pyridyl)-1,3-propanedione, 1-oxime and 1-cyclopropyl-3-(3-pyridyl)-1,3-propanedione, 3-oxime (Examples 9 and 10) with stirring at room temperature. The reaction is stirred at room temperature for 20 minutes and then poured onto cracked ice. The mixture is diluted with water, made basic with aqueous sodium hydroxide and extracted with chloroform. The chloroform solution is dried over magnesium sulfate and concentrated under reduced pressure to give a cream-colored solid. This solid is recrystallized from hexane to yield white crystals, melting point 73°–77°C., which is a mixture of 3-(5-cyclopropyl-3-isoxazolyl)pyridine and 3-(3-cyclopropyl-5-isoxazoly)pyridine. Treatment of the mixture by liquid-liquid partition chromatography on a diatomaceous earth column with a heptane-acetonitrile system affords separation of the components; namely, 3-(5-cyclopropyl-3-isoxazolyl)pyridine as white crystals, melting point 74°–75°C., nmr spectrum δ6.82 (DMSO-$d_6$, s, 4-isoxazolyl H); 3-(3-cyclopropyl-5-isoxazolyl)-pyridine as white crystals, melting point 73°–75°C., nmr spectrum δ6.92 (DMSO-$d_6$, s, 4-isoxazolyl H).

The 3-(5-cyclopropyl-3-isoxazolyl)pyridine provides a slightly soluble acetate salt when treated with acetic acid and 3-(3-cyclopropyl-5-isoxazolyl)pyridine gives a water soluble sulfate salt following treatment with sulfuric acid.

EXAMPLES 13 and 14

Preparation of 3-(5-Cyclopropyl-3-isoxazolyl)pyridine and 3-Amino-3-cyclopropyl-1-(3-pyridyl)-2-propen-1-one A 1.0 g. sample of the mixture of 3-(5-cyclopropyl-3-isoxazolyl)pyridine and 3-(3-cyclopropyl-5-isoxazolyl)pyridine, obtained as described in Examples 11 and 12, is mixed with 0.143 g. of platinum oxide and 75 ml. of ethanol. This mixture is treated with hydrogen on a Parr apparatus at 40 psi for 2 hours at room temperature. The mixture is filtered and the filtrate concentrated to yield a tacky, brown solid. The solid is dissolved in methanol and placed on preparative silica gel thin layer chromatographic plates and developed with 15% methanol-benzene. The least polar band is extracted to give 3-(5-cyclopropyl-3-isoxazolyl)pyridine as off-white crystals, melting point 70°–73°C. and the nmr spectrum δ6.82 (DMO-$d_6$, s, 4-isoxazolyl H). The more polar fraction is extracted to give a viscous liquid. The 3-amino-3-cyclopropyl-1-(3-pyridyl)-2-propen-1-one is characterized as the diperchlorate salt, white crystals, melting point, 149°–154°C.

EXAMPLE 15

Preparation of 3-[5-Cyclopropyl-5-(1-pyrrolidinyl)-2-isoxazolin-3-yl]pyridine

To a rapidly stirred solution containing 33.6 g. of 1-(1-cyclopropylvinyl)pyrrolidine and 24.2 g. of triethylamine in 500 ml. of absolute ethanol is added in small portions, over a 0.5 hour period, 15.4 g. of nicotinoyl chloride, oxime hydrochloride. The reaction is stirred 2 hours at room temperature and then the solvent is removed under reduced pressure. The residue is dissolved in chloroform, washed three times with water, and the organic layer is dried over sodium sulfate. Removal of the solvent leaves a solid, which is recrystallized from hexane to give white needles, melting point 90°–92°C.

EXAMPLE 16

Preparation of 3-(5-Cyclopropyl-3-isoxazolyl)pyridine

A solution containing 1.43 g. of perchloric acid (70%) in 5 ml. of absolute ethanol is added dropwise with stirring to a solution of 2.57 g. of 3-[5-cyclopropyl-5-(1-pyrrolidinyl)-2-isoxazolin-3-yl]-pyridine in 25 ml. of absolute ethanol. The resulting solution is diluted with 25 ml. of water and then heated vigorously on a steam bath for 0.5 hours. The hot solution is poured directly onto 200 g. of ice. The precipitate is collected by filtration, washed well with water and air dried. This gives a white solid, melting point 72°–75°C. and the nmr spectrum δ6.82 (DMSO-$d_6$, s, 4-isoxazolyl H).

EXAMPLE 17

Preparation of 3-(5-Cyclopropyl-3-isoxazolyl)pyridine

To a stirred mixture containing 1.35 g. of nicotinoyl chloride oxime hydrochloride and 2.6 g. of 1-iodovinyl-cyclopropane in 50 ml. of ethanol is added dropwise over a 1 hour period, a solution of 4.27 g. of triethylamine in 40 ml. of ethanol. The reaction is stirred for 1 hour and then the solvent is removed under reduced pressure. The residue is dissolved in water and ether and the ether layer is separated. The water layer is extracted twice with ether and then the combined ether layers are dried over sodium sulfate. Filtration and removal of the solvent under reduced pressure gives an orange-yellow solid. This material is recrystallized from isopropyl alcohol to give white crystals, melting point 74°–75°C., nmr spectrum δ6.82 (DMSO-$d_6$, s, 4-isoxazolyl H).

EXAMPLE 18

Preparation of 1-Cyclopropyl-3-(2-pyridyl)-1,3-propanedione

A stirred mixture of 24 g. of ethyl picolinate, 18 g. of cyclopropylmethyl ketone and 11 g. of sodium methoxide in 250 ml. of benzene is heated under reflux for 6 hours. The mixture is diluted with 200 ml. of water and the water phase is removed. The aqueous solution is made weakly acidic with dilute hydrochloric acid. A solid precipitates and is collected by filtration. Recrystallization from cyclohexane provided colorless crystals, melting point 77°–78°C.

EXAMPLES 19 and 20

Preparation of 1-Cyclopropyl-3-(2-pyridyl)-1,3-propanedione, 1-Oxime and 1-Cyclopropyl-3-(2-pyridyl)-1,3-propanedone, 3-Oxime A solution of 1.9 g. of 1-cyclopropyl-3-(2-pyridyl)-1,3-propanedione, 0.695 g. of hydroxylamine hydrochloride and 2.0 g. of triethylamine in 25 ml. of ethanol is heated under reflux for 5 hours. The reaction mixture is concentrated under reduced pressure and the residue is partially dissolved in 10 ml. of water. The aqueous mixture is extracted with chloroform, the chloroform solution is dried over magnesium sulfate and concentrated under reduced pressure to give the mixture of 1-cyclopropyl-3-(2-pyridyl)-1,3-propanedione, 1-oxime and 1-cyclopropyl-3-(2-pyridyl)-1,3-propanedione, 3-oxime as a viscous liquid. This liquid is used in Examples 21 and 22 without further purification.

EXAMPLES 21 and 22

Preparation of 2-(5-Cyclopropyl-3-isoxazolyl)pyridine hydrochloride and 2-(Cyclopropyl-5-isoxazolyl)pyridine hydrochloride A mixture of 0.354 g. of the mixture of 1-cyclopropyl-3-(2-pyridyl)-1,3-propanedione, 1-oxime and 1-cyclopropyl-3-(2-pyridyl)-1,3-propanedione, 3-oxime (Examples 19 and 20) and 1.0 ml. of concentrated sulfuric acid is stirred for 20 minutes. This mixture is poured onto cracked ice and diluted with 50 ml. of water. The aqueous solution is made basic with 10N sodium hydroxide and extracted with chloroform. The chloroform solution is dried over magnesium sulfate and concentrated under reduced pressure to yield a yellow, mobile liquid. The liquid is dissolved in ethanol and acidified with ethanolic hydrogen chloride. Addition of ether precipitates a white solid, which is collected and recrystallized from acetonitrile to provide 2-(5-cyclopropyl-3-isoxazolyl)pyridine hydrochloride and 2-(3-cyclopropyl-5-isoxazolyl)pyridine hydrochloride as white crystals, melting point 159°–162°C. Treatment of this mixture as the free base by liquid-liquid partition chromatography on a diatomaceous earth column with a heptane-acetonitrile system affords separation of the components; namely, 2-(5-cyclopropyl-3-isoxazolyl)pyridine, characterized as the hydrochloride, white crystals, melting point 132°–136°C., nmr spectrum δ6.79 (DMSO-$d_6$, s, 4-isoxazolyl H); and 2-(3-cyclopropyl-5-isoxazolyl)pyridine, characterized as the hydrochloride, melting point 164°–168°C., nmr spectrum δ6.88 (DMSO-$d_6$, s, 4-isoxazolyl H).

EXAMPLES 23, 24 and 25

Preparation of 2-(5-Cyclopropyl-3-isoxazolyl)pyridine hydrochloride, 3-Amino-1-cyclopropyl-3-(2-pyridyl)-2-propen-1-one perchlorate and 3-Amino-3-cyclopropyl-1-(2-pyridyl)-2-propen-1-one picrate An 8.3 g. sample of a mixture of 2-(5-cyclopropyl-3-isoxazolyl)pyridine hydrochloride and 2-(3-cyclopropyl-5-isoxazolyl)pyridine hydrochloride, obtained as described in Examples 21 and 22, is dissolved in aqueous sodium hydroxide and extracted with chloroform. The chloroform solution is dried over magnesium sulfate and concentrated to give a viscous liquid. The liquid is dissolved in 100 ml. of ethanol, 0.9 g. of platinum oxide added and the mixture treated with hydrogen on a Parr apparatus at 43 psi for 2.0 hours. The mixture is filtered and the filtrate concentrated to give a brown liquid. The liquid is dissolved in methanol and placed on silica gel preparative thin layer chromatographic plates and developed with 10% methanol-benzene. The least polar band is extracted to give a brown liquid. The liquid is dissolved in ethanol and acidified with ethanolic hydrogen chloride. Addition of ether precipitates a solid which is collected to provide 2-(5-cyclopropyl-3-isoxazolyl)pyridine hydrochloride as off-white crystals, nmr spectrum δ6.77 (DMSO-$d_6$, s, 4-isoxazolyl H). The most polar band is extracted to give a tacky solid. The solid is dissolved in ethanol and acidified with 70% perchloric acid. Addition of water precipitates a solid, which is collected and recrystallized from ethanol to afford 3-amino-1-cyclopropyl-3-(2-pyridyl)-2-propen-1-one perchlorate as yellow crystals, melting point 187°–188°C. The middle band is extracted to give a brown liquid, which is dissolved in ethanol and acidified with ethanolic picric acid. The crystals which form are collected and recrystallized from ethanol to give 3-amino-3-cyclopropyl-1-(2-pyridyl)-2-propen-1-one picrate as light brown crystals, melting point 145°–150°C.

EXAMPLE 26

Preparation of 2-(5-Cyclopropyl-3-isoxazolyl)pyridine hydrochloride

A solution containing 2.01 g. of a mixture of the monooximes of 1-cyclopropyl-3-(2-pyridyl)-1,3-propanedione and 3 drops of 2.3N ethanolic hydrogen chloride in 35 ml. of ethanol is heated for one-half hour on a steam bath. The solvent is removed under reduced pressure and the residue is dissolved in chloroform. The chloroform layer is washed with water and then dried over sodium sulfate. Removal of the solvent under reduced pressure gives an oil, nmr spectrum $\delta 6.78$ (DMSO-$d_6$, s, 4-isoxazolyl H) characterized as the hydrochloride, white crystals melting point 134°–137°C.

EXAMPLE 27

Preparation of 1-Cyclopropyl-3-(2-pyrazinyl)-1,3-propanedione

A stirred mixture of 14.0 g. of methyl pyrazinoate, 16.8 g. of cyclopropylmethyl ketone, 6.0 g. of sodium methoxide and 200 ml. of benzene is heated under reflux for 5 hours. A 400 ml. volume of water is added to the mixture. The benzene phase is separated and the aqueous solution is made weakly acidic with dilute hydrochloric acid. A yellow solid precipitates, which is collected and recrystallized from hexane to give white crystals, m.p. 111°–112°C.

EXAMPLES 28 and 29

Preparation of 1-Cyclopropyl-3-(2-pyrazinyl)-1,3-propanedione, 1-oxime and 1-Cyclopropyl-3-(2-pyrazinyl)-1,3-propanedione, 3-oxime A mixture of 100 g. of 1-cyclopropyl-3-(2-pyrazinyl)-1,3-propanedione, 36 g. of hydroxylamine hydrochloride and 111.7 g. of triethylamine in 1000 ml. of ethanol is heated under reflux for 7 hours. The ethanol is evaporated under reduced pressure and the residue is mixed with 500 ml. of water. The aqueous mixture is extracted with chloroform and the chloroform solution dried over magnesium sulfate. The chloroform solution is concentrated under reduced pressure to furnish a viscous, brown liquid. The liquid is used in Examples 30 and 31 without further purification.

EXAMPLES 30 and 31

Preparation of 2-(5-Cyclopropyl-3-isoxazolyl)pyrazine and 2-(3-Cyclopropyl-5-isoxazolyl)pyrazine A mixture of 1.0 g. of 1-cyclopropyl-3-(2-pyrazinyl)-1,3-propanedione, 1 and 3 oxime (Examples 28 and 29) and 5.0 ml. of concentrated sulfuric acid is stirred at room temperature for 25 minutes. The solution is poured onto cracked ice and diluted with 200 ml. of water. The mixture is made basic with 10N sodium hydroxide. The basic mixture is extracted with chloroform and the chloroform solution dried over magnesium sulfate. The chloroform solution is concentrated under reduced pressure to provide an off-white solid which is recrystallized from ethanol to give white crystals, m.p. 106°–109°C., which is a mixture of 2-(5-cyclopropyl-3-isoxazolyl)pyrazine and 2-(3-cyclopropyl-5-isoxazolyl)pyrazine. Separation of this mixture by liquid-liquid partition chromatography on a diatomaceous earth column with a heptane-acetonitrile system provides 2-(5-cyclopropyl-3-isoxazolyl)pyrazine, as white crystals, m.p. 80°–81°C., nmr spectrum $\delta 6.78$ (DMSO-$d_6$, s, 4-isoxazolyl H) and of 2-(3-cyclopropyl-5-isoxazolyl)pyrazine as white crystals, m.p. 99°–100°C., nmr spectrum $\delta 7.02$ (DMSO-$d_6$, s, 4-isoxazolyl H).

EXAMPLE 32

Preparation of 2-(5-Cyclopropyl-3-isoxazolyl)pyrazine

A solution containing 2.05 g. of a mixture of the mono-oximes of 1-cyclopropyl-3-(2-pyrazinyl)-1,3-propanedione (Examples 28 and 29) and 2 drops of 2.3N ethanolic hydrogen chloride in 35 ml. of ethanol is heated for 0.5 hours on a steam bath. The solvent is removed under reduced pressure and the solid residue is shaken with water, filtered, and air dried. This gives white crystals, melting point 86°–91°C., nmr spectrum $\delta 6.78$ (DMSO-$d_6$, s, 4-isoxazolyl H).

EXAMPLES 33 and 34

Preparation of 2-(5-Cyclopropyl-3-isoxazolyl)pyrazine and 1-Amino-3-cyclopropyl-1-(2-pyrazinyl)-2-propen-3-one A 17 g. sample of the mixture of 2-(5-cyclopropyl-3-isoxazolyl)pyrazine and 2-(3-cyclopropyl-5-isoxazolyl)pyrazine, obtained as described in Examples 30 and 31, is mixed with 250 ml. of ethanol and 1.7 g. of platinum oxide. This mixture is treated with hydrogen on a Parr apparatus at 48 psi. for 2 hours at room temperature. The mixture is filtered and the filtrate concentrated under reduced pressure to give a brown tar. This tar is dissolved in methanol and placed on preparative silica gel thin layer chromatographic plates and developed with 10% methanol-benzene. The least polar band is extracted to give 2-(5-cyclopropyl-3-isoxazolyl)pyrazine as white crystals, melting point 80°–82°C., nmr spectrum $\delta 6.77$ (DMSO-$d_6$, s, 4-isoxazolyl H). The most polar band is extracted to yield the 1-amino-3-cyclopropyl-1-(2-pyrazinyl)-2-propen-3-one as a light brown solid which is recrystallized from acetonitrile to give dull yellow crystals, melting point 146°–150° C.

EXAMPLE 35

Preparation of 1-cyclopropyl-3-(3-pyridazinyl)-1,3-propanedione

A stirred mixture of 4.0 g. of ethyl-3-pyridazinecarboxylate, 4.4 g. of cyclopropylmethyl ketone and 1.6 g. of sodium methoxide in 100 ml. of benzene is heated under reflux for 5 hours. The mixture is diluted with 300 ml. of water and the benzene phase is separated. The aqueous mixture is made weakly acidic with dilute hydrochloric acid and extracted with chloroform. The chloroform solution is dried over magnesium sulfate and concentrated under reduced pressure to yield straw-colored crystals which are recrystallized from acetonitrile to give cream-colored crystals, melting point 85°–87°C.

EXAMPLES 36 and 37

Preparation of
1-Cyclopropyl-3-(3-pyridazinyl)-1,3-propanedione-1-oxime and
1-Cyclopropyl-3-(3-pyridazinyl)-1,3-propanedione-3-oxime A solution of 1.9 g. of the 1-cyclopropyl-3-(3-pyridazinyl)-1,3-propanedione, 0.70 g. of hydroxylamine hydrochloride and 2.0 g. of triethylamine in 25 ml. of ethanol is heated under reflux for 6 hours. The mixture was concentrated under reduced pressure to an oily, solid reside, which is mixed with 50 ml. of water and made basic with 10N sodium hydroxide. The aqueous mixture is extracted with chloroform and the chloroform solution is dried over magnesium sulfate. The chloroform solution is concentrated under reduced pressure to furnish a light brown solid, which is recrystallized from acetonitrile to provide white crystals, melting point 135°–137°C.

EXAMPLES 38 and 39

Preparation of
3-(5-Cyclopropyl-3-isoxazolyl)pyridazine and
3-(3-Cyclopropyl-5-idoxazolyl)pyridazine To 2.8 g. of a mixture of 1-cyclopropyl-3-(3-pyridazinyl)-1,3-propanedione-1 and 3-oximes is added cautiously 5.0 ml. of concentrated sulfuric acid and the mixture is stirred at room temperature for 20 minutes. The mixture is poured onto cracked ice, diluted with 100 ml. of water and then made basic with 10N sodium hydroxide. The aqueous mixture is extracted with chloroform, the chloroform solution dried over magnesium sulfate and concentrated under reduced pressure to give a brown solid, which is recrystallized from isopropyl alcohol to furnish light brown crystals, melting point 130°–132°C., a mixture of 3-(5-cyclopropyl-3-isoxazolyl)pyridazine and 3-(3-cyclopropyl-5-isoxazolyl)pyradizine. Treatment of this mixture by liquid-liquid partition chromatography on a diatomaceous earth column with a heptane-ethyl acetate-methanol-water system affords separation of the components; namely, 3-(5-cyclopropyl-3-isoxazolyl)-pyridazine as off-white crystals, melting point 105°–107°C. nmr spectrum δ6.91 (DMSO-d$_6$, s, 4-isoxazolyl H) and 3-(3-cyclopropyl-5-isoxazolyl)pyridazine as off-white crystals, melting point 141°–142°C., nmr spectrum δ7.12 (DMSO-d$_6$, s, 4-isoxazolyl H).

EXAMPLE 40

Preparation of
3-(5-Cyclopropyl-3-isoxazolyl)pyridazine

To a stirred mixture of 1.7 g. of a mixture of 1-cyclopropyl-3-(3-pyridazinyl)-1,3-propanedione, 1-and 3-oximes (Examples 36 and 37) in 10 ml. of methylene chloride is added 2.0 ml. of concentrated sulfuric acid dropwise with ice-bath cooling. The mixture is stirred with ice-bath cooling for 20 minutes and then poured onto cracked ice. The aqueous mixture is made basic with 10N sodium hydroxide and extracted with chloroform. The chloroform solution is dried over magnesium sulfate and concentrated under reduced pressure to give straw-colored crystals, melting point 101°–105°C., nmr spectrum δ6.90 (DMSO-d$_6$, s, 4-isoxazolyl H).

EXAMPLE 41

Preparation of
1-Cyclopropyl-3-(4-pyrimidinyl)-1,3-propanedione

A stirred mixture of 1.4 g. of methyl-4-pyrimidinecarboxylate, 1.7 g. of cyclopropylmethyl ketone, 1.2 g. of sodium methoxide and 40 ml. of benzene is heated under reflux for 4 hours. The mixture is diluted with 40 ml. of water and the benzene phase is removed. The aqueous mixture is made weakly acidic with dilute hydrochloric acid and extracted with chloroform. The cloroform solution is dried over magnesium sulfate and concentrated under reduced pressure to give light brown crystals, which are recrystallized from hexane to provide straw-colored crystals, melting point 81°–84°C.

EXAMPLES 42 and 43

Preparation of
1-Cyclopropyl-3-(4-pyrimidinyl)-1,3-propanedione, 1-oxime and
1-Cyclopropyl-3-(4-pyrimidinyl)-1,3-propanedione, 3-oxime A solution of 3.0 g. of 1-cyclopropyl-3-(4-pyrimidinyl)-1,3-propanedione, 1.1 g. of hydroxylamine hydrochloride and 3.2 g. of triethylamine is heated under reflux for 5 hours. The ethanol is evaporated under reduced pressure and the residue is mixed with water. The aqueous mixture is extracted with chloroform, the chloroform solution dried over magnesium sulfate and concentrated under reduced pressure to give 3.2 g. of a viscous brown liquid. This liquid is used in Examples 44 and 45 without further purification.

EXAMPLES 44 and 45

Preparation of
4-(5-Cyclopropyl-3-isoxazolyl)pyrimidine and
4-(3-Cyclopropyl-5-isoxazolyl)pyrimidine To a stirred solution of 10.5 g. of a mixture of 1-cyclopropyl-3-(4-pyrimidinyl)-1,3-propanedione, 1-and 3-oximes in 30 ml. of methylene chloride is added 10.0 ml. of concentrated sulfuric acid dropwise during 10 minutes with ice-bath cooling. The mixture is poured onto cracked ice, made basic with 10N sodium hydroxide and extracted with chloroform. The chloroform solution is dried over magnesium sulfate and concentration under reduced pressure to furnish light brown crystals, melting point 65°–80°C., which is a mixture of 4-(5-cyclopropyl-3-isoxazolyl)pyrimidine and 4-(3-cyclopropyl-5-isoxazolyl)pyrimidine. Treatment of this mixture by liquid-liquid partition chromatography on a diatomaceous earth column with a heptane-acetonitrile system affords separation of the components; namely, 4-(5-cyclopropyl-3-isoxazolyl)-pyrimidine as cream-colored crystals, melting point 63°–68°C., nmr spectrum δ6.81 DMSO-d₆, s, 4-isoxazolyl H) and 4-(3-cyclopropyl-5-isoxazolyl)pyrimidine as straw-colored crystals, melting point 110°–114°C., nmr spectrum δ7.13 (DMSO-d₆, s, 4-isoxazolyl H).

EXAMPLE 46

Preparation of
1-Cyclopropyl-3-(2-quinoxalinyl)-1,3-propanedione

A mixture of 3.0 g. of ethyl-2-quinoxalate, 1.7 g. of cyclopropylmethyl ketone and 0.9 g. of sodium methoxide in 100 ml. of benzene is heated under reflux for 4 hours. The mixture is diluted with 100 ml. of water and the benzene phase is separated. The aqueous solution is made weakly acidic with dilute hydrochloric acid and extracted with chloroform. The chloroform solution is dried over magnesium sulfate and concentrated under reduced pressure to yield straw-colored crystals, which are recrystallized from acetonitrile to provide cream-colored crystals, melting point 113°–115°C.

EXAMPLES 47 and 48

Preparation of
1-Cyclopropyl-3-(2-quinoxalinyl)-1,3-propanedione, 1-oxime and
1-Cyclopropyl-3-(2-quinoxalinyl)-1,3-propanedione, 3-oxime A stirred mixture of 9.6 g. of 1-cyclopropyl-3-(2-qunioxalinyl)-1,3-propanedione, 2.8 g. of hydroxylamine hydrochloride and 8.2 g. of triethylamine in 100 ml. of ethanol is heated under reflux for 5 hours. The ethanol is evaporated under reduced pressure and the residue is mixture with 100 ml. of water. The aqueous mixture is extracted with chloroform, the chloroform solution is dried over magnesium sulfate and concentrated under reduced pressure to give a brown tar. This tar is used in Examples 49 and 50 without further purification.

EXAMPLES 49 and 50

Preparation of
2-(5-Cyclopropyl-3-isoxazolyl)quinoxaline and
2-(3-Cyclopropyl-5-isoxazolyl)quinoxaline To a stirred solution of 9.0 g. of a mixture of 1-cyclopropyl-3-(2-quinoxalinyl)-1,3-propanedione, 1- and 3-oximes (Examples 47 and 48) in 100 ml. of methylene chloride is added 20 ml. of concentrated sulfuric acid dropwise during 12 minutes with ie-bath cooling. The mixture is stirred at room temperature for 30 minutes and then poured onto cracked ice and made basic with 10N sodium hydroxide. The mixture is extracted with methylene chloride, the methylene chloride solution is dried over magnesium sulfate and concentrated under reduced pressure to give a light brown solid, which is recrystallized from acetonitrile to provide dull yellow crystals, melting point 98°–104°C. This is a mixture of 60% 2-(5-cyclopropyl-3-isoxazolyl)quinoxaline, nmr spectrum δ6.92 (DMSO-d₆, 4-isoxazolyl H) and 40% 2-(3-cyclopropyl-5-isoxazolyl)quinoxaline, nmr spectrum δ7.27 (DMSO-d₆, s, 4-isoxazolyl H), which is used in Examples 51, 52 and 53.

EXAMPLES 51, 52 and 53

Preparation of
2-(5-Cyclopropyl-3-isoxazolyl)quinoxaline and
1-Amino-1-cyclopropyl-3-(2-quinoxalinyl)-2-propen-3-one Picrate and
3-Amino-1-cyclopropyl-3-(2-quinoxalinyl)-2-propen-1-one Picrate A 2.4 g. sample of a mixture of 2-(5-cyclopropyl-3-isoxazolyl)quinoxaline and 2-(3-cyclopropyl-5-isoxazolyl)quinoxaline (Examples 49 and 50) is mixed with 0.3 g. of platinum oxide and 75 ml. of ethanol and treated with hydrogen on a Parr apparatus at 43 psi, for 2 hours at room temperature. The mixture is filtered and the filtrate concentrated under reduced pressure to give a brown tar. The tar is dissolved in methanol and placed on preparative silica gel thin layer chromatographic plates and developed with 10% methanol-benzene. The least polar band is extracted to yield a yellow solid, which is recrystallized from acetonitrile to provide yellow crystals of 2-(5-cyclopropyl-3-isoxazolyl)quinoxaline, melting point 108°–112°C., nmr spectrum δ6.91 (DMSO-d₆, s, 4-isoxazolyl H). The most polar band is extracted to give a brown glassy solid. This solid is dissolved in ethanol and acidified with ethanolic picric acid, a solid forms and is collected to provide 1-amino-1-cyclopropyl-3-(2-quinoxalinyl)-2-propen-3-one picrate as light brown crystals, melting point 150°–152°C. The middle band is extracted to give a tacky brown solid. This solid is dissolved in ethanol and acidified with ethanolic picric acid, a solid forms and is collected to provide 3-amino-1-cyclopropyl-3-(2-quinoxalinyl)-2-propen-1-one picrate as light brown crystals, melting point 153°–157°C.

EXAMPLE 54

Preparation of
4-(5-Cyclopropyl-2-isoxazolin-3-yl)pyridine

To a stirred mixture containing 3.8 g. of isonicotinoyl chloride, oxime hydrochloride and 1.4 g. of vinylcyclopropane in 100 ml. of ethanol is added dropwise over a 1 hour period, a solution 4.1 g. of triethylamine in 40 ml. of ethanol. The reaction is stirred for 1 hour and then the solvent is removed under reduced pressure. The residue is extracted with ether and the ether solution is dried over sodium sulfate. The solution is filtered and then the solvent is removed giving a yellow solid. The solid is recrystallized from ethanol giving white crystals, melting point 102°–108°C.

EXAMPLE 55

Preparation of
3-(5-Cyclopropyl-2-isoxazolin-3-yl)pyridine Hydrochloride

To a stirred mixture containing 4.82 g. of nicotinoyl chloride, oxime hydrochloride and 1.7 g. of vinylcyclopropane in 100 ml. of ethanol is added dropwise over a 1 hour period a solution of 5.1 g. of triethylamine in 80 ml. of ethanol. The reaction is stirred for 1 hour and then the solvent is removed under reduced pressure. The residue is dissolved in water and ether, and the ether layer separated. The water layer is extracted with ether and the ether solution is dried over sodium sulfate. Addition of hydrogen chloride gas gives a yellow-white solid, which is recrystallized from methanol to give white crystals, melting point 199°–203°C.

We claim:
1. A cyclopropylisoxazole of the formula:

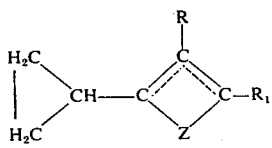

wherein R is a member of a group consisting of hydrogen, lower alkyl, lower cycloalkyl and phenyl; $R_1$ is pyridyl; Z is a trivalent radical selected from the group consisting of A and B

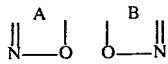

and the dotted line represents one double bond, the position being dependent upon the definition of Z and when Z is B, the double bond is adjacent to the cyclopropyl substituent and when Z is A, the double bond is in the other position with the proviso that when Z is B and R is as defined above the carbon to carbon double bond may also be absent, and a pharmaceutically acceptable salt thereof.

2. The cyclopropylisoxazole in accordance with claim 1, 3-(5-cyclopropyl-3-isoxazolyl)pyridine.

3. The cyclopropylisoxazole in accordance with claim 1, 4-(5-cyclopropyl-3-isoxazolyl)pyridine.

4. The cyclopropylisoxazole in accordance with claim 1, 2-(5-cyclopropyl-3-isoxazolyl)pyridine hydrochloride.

5. The cyclopropylisoxazole in accordance with claim 1, 2-(3-cyclopropyl-5-isoxazolyl)pyridine hydrochloride.

6. The cyclopropylisoxazole in accordance with claim 1, 4-(3-cyclopropyl-5-isoxazolyl)pyridine.

7. The cyclopropylisoxazole in accordance with claim 1, 4-(5-cyclopropyl-2-isoxazolin-3-yl)pyridine.

8. The cyclopropylisoxazole in accordance with claim 1, 3-(5-cyclopropyl-2-isoxazolin-3-yl)pyridine.

9. The cyclopropylisoxazole in accordance with claim 1, 3-(3-cyclopropyl-5-isoxazolyl pyridine.

10. The cyclopropylisoxazole in accordance with claim 1, 2-(5-cyclopropyl-4-methyl-3-isoxazolyl)pyridine.

11. The cyclopropylisoxazole in accordance with claim 1, 3-(5-cyclopropyl-4-methyl-3-isoxazolyl)pyridine.

12. The cyclopropylisoxazole in accordance with claim 1, 4-(5-cyclopropyl-4-ethyl-3-isoxazolyl)pyridine.

13. The cyclopropylisoxazol in accordance with claim 1, 2-(4,5-dicyclopropyl-3-isoxazdyl)pyridine.

14. The cyclopropylisoazol in accordance with claim 1, 3-(4,5-dicyclopropyl-3-isoxazolyl)pyridine.

15. The cyclopropylisoxazol in accordance with claim 1, 4-(5-cyclopropyl-2-isoxazolin-3-yl)pyridine.

16. The cyclopropylisoxazol in accordance with claim 1, 2-(5-cyclopropyl-4-methyl-2-ioxazolin-3-yl)pyridine.

17. The cyclopropylisoxazol in accordance with claim 1, 3-(5-cyclopropyl-4-phenyl-3-isoxazolyl)pyridine.

18. The cyclopropylisoxazol in accordance with claim 1, 4-(5-cyclopropyl-4-phenyl-2-isoxazolin-3-yl)pyridine.

19. The cyclopropylisoxazol in accordance with claim 1, 2-(5-cyclopropyl-2-isoxazolin-3-yl)pyridine.

20. The cyclopropylisoxazol in accordance with claim 1, 3-(4,5-dicyclopropyl-2-isoxazolin-3-yl)pyridine.

21. The cyclopropylisoxazol in accordance with claim 1, 2-chloro-3-(5-cyclopropyl-3-isoxazolyl)pyridine.

22. The cyclopropylisoxazol in accordance with claim 1, 3-[cyclopropyl-5-(1-pyrrolidinyl)-2-isoxazolin-3-yl]pyridine.

23. The cyclopropylisoxazol in accordance with claim 1, 3-(5-cyclopropyl-2-isoxazolin-3-yl)pyridine hydrochloride.

24. The cyclopropylisoxazol in accordance with claim 1, 4-(5-cyclopropyl-5-(1-pyrrolidinyl)-2-isoxazolin-3-yl)pyridine.

25. The cyclopropylisoxazol in accordance with claim 1, 6-methyl-2-(5-cyclopropyl-3-isoxazolyl)pyridine.

26. The cyclopropylisoxazol in accordance with claim 1, 6-methyl-2-(3-cyclopropyl-5-isoxazolyl)pyridine.

* * * * *